(12) United States Patent
Wright et al.

(10) Patent No.: US 11,613,286 B2
(45) Date of Patent: Mar. 28, 2023

(54) CART FOR MEDICAL EQUIPMENT

(71) Applicant: Covidien LP, Mansfield, MA (US)

(72) Inventors: Mark Wright, Carlsbad, CA (US); Matthew Phillips, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 91 days.

(21) Appl. No.: 17/005,056

(22) Filed: Aug. 27, 2020

(65) Prior Publication Data

US 2021/0070338 A1   Mar. 11, 2021

Related U.S. Application Data (60) Provisional application No. 62/897,079, filed on Sep. 6, 2019.

(51) Int. Cl.
*B62B 3/02* (2006.01)
*A61B 50/13* (2016.01)

(52) U.S. Cl.
CPC ............... *B62B 3/02* (2013.01); *A61B 50/13* (2016.02)

(58) Field of Classification Search
CPC .................................. B62B 3/02; A61B 50/13
See application file for complete search history.

(56) References Cited

U.S. PATENT DOCUMENTS

| | | | | |
|---|---|---|---|---|
| 3,840,265 A | * | 10/1974 | Stirling | A61G 3/006 296/19 |
| 4,578,833 A | * | 4/1986 | Vrzalik | A61G 7/008 128/869 |
| 5,170,804 A | | 12/1992 | Glassman | |
| 5,337,845 A | * | 8/1994 | Foster | A61G 7/00 180/11 |
| 5,370,111 A | * | 12/1994 | Reeder | A61G 7/05 128/202.13 |
| 5,518,310 A | | 5/1996 | Ellman et al. | |
| 6,102,497 A | * | 8/2000 | Ehr | A61G 12/001 280/47.35 |
| 6,251,113 B1 | * | 6/2001 | Appelbaum | A61B 17/00 604/22 |
| D459,477 S | | 6/2002 | Stocks et al. | |
| 6,626,445 B2 | | 9/2003 | Murphy et al. | |
| 6,669,639 B1 | | 12/2003 | Miller et al. | |
| D486,915 S | | 2/2004 | Warschewske et al. | |

(Continued)

FOREIGN PATENT DOCUMENTS

CN    101994677 A  *  3/2011

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Erez Gurari (57) ABSTRACT

A cart for medical equipment includes a base having one or more wheels, a column supported by the base, and a platform supported on the column and opposite the base. The platform is configured to mount a piece of medical equipment to the cart. The cart also includes an adapter plate securable to the piece of medical equipment and configured to releasably couple to the platform. The adapter plate includes a locking assembly having one or more handles that upon actuation releases the adapter plate from the platform.

19 Claims, 6 Drawing Sheets

(56) References Cited

U.S. PATENT DOCUMENTS

| | | | |
|---|---|---|---|
| D492,856 S | 7/2004 | Rossini et al. | |
| D493,042 S | 7/2004 | Rossini et al. | |
| D493,977 S | 8/2004 | Rossini et al. | |
| D500,575 S | 1/2005 | Lucas | |
| 6,980,419 B2 | 12/2005 | Smith et al. | |
| D518,267 S | 3/2006 | Arceta | |
| D534,746 S | 1/2007 | Rossini et al. | |
| D535,509 S | 1/2007 | Rossini et al. | |
| D539,794 S | 4/2007 | Rossini et al. | |
| D544,962 S | 6/2007 | Diener et al. | |
| D548,918 S | 8/2007 | Nussberger | |
| 7,594,668 B2 | 9/2009 | Arceta et al. | |
| 7,828,253 B2* | 11/2010 | Meyer | A47B 21/00 248/129 |
| 8,109,527 B2* | 2/2012 | Bustle | A47B 21/0314 280/47.35 |
| 10,076,838 B1* | 9/2018 | Martinez | H01B 13/012 |
| 10,426,261 B2* | 10/2019 | Theis | E05B 73/0082 |
| 10,453,572 B1* | 10/2019 | Brooks | G16H 40/40 |
| 10,617,299 B2* | 4/2020 | Sanchez | H04N 7/142 |
| 10,646,033 B2* | 5/2020 | Lindblad | F16M 11/2014 |
| 10,749,359 B2* | 8/2020 | Ross | H02J 4/00 |
| D923,799 S * | 6/2021 | St. Pierre | D24/185 |
| D933,835 S * | 10/2021 | St. Pierre | D24/185 |
| 2004/0186357 A1* | 9/2004 | Soderberg | A61B 5/02055 600/300 |
| 2004/0262867 A1* | 12/2004 | Arceta | A61G 12/001 280/47.35 |
| 2005/0288571 A1* | 12/2005 | Perkins | A61B 90/50 600/407 |
| 2006/0163829 A1* | 7/2006 | Livengood | A61B 50/13 280/87.021 |
| 2008/0084147 A1* | 4/2008 | Brown | A47B 83/001 312/223.3 |
| 2008/0252045 A1* | 10/2008 | Rossini | B62B 3/02 280/659 |
| 2009/0212744 A1* | 8/2009 | Werthman | H02J 7/0027 320/162 |
| 2010/0000447 A1* | 1/2010 | Song | A61B 5/00 108/50.11 |
| 2010/0148458 A1* | 6/2010 | Ross | A61M 16/021 280/47.34 |
| 2011/0025007 A1* | 2/2011 | Butler | A61G 12/001 280/47.35 |
| 2011/0232535 A1* | 9/2011 | Hung | A61B 50/13 108/25 |
| 2012/0236496 A1* | 9/2012 | McRorie | F16M 11/046 361/679.55 |
| 2013/0200579 A1* | 8/2013 | Abernethy | B62B 5/04 280/6.15 |
| 2014/0265193 A1* | 9/2014 | Stark | F16M 11/08 280/47.34 |
| 2015/0105660 A1* | 4/2015 | Ninomiya | A61B 8/4405 600/437 |
| 2015/0223890 A1* | 8/2015 | Miller | G06F 21/6245 705/2 |
| 2015/0223892 A1* | 8/2015 | Miller | A61B 50/10 345/174 |
| 2015/0342562 A1* | 12/2015 | Messina | F16M 11/043 248/544 |
| 2016/0006992 A1* | 1/2016 | Roberts | H04N 5/23293 348/113 |
| 2017/0341666 A1* | 11/2017 | Carzola | B62B 3/004 |
| 2018/0201289 A1* | 7/2018 | Sakakibara | B62B 5/00 |
| 2018/0325500 A1* | 11/2018 | Shuart | A61B 10/0233 |
| 2018/0325762 A1* | 11/2018 | Hazzard | E05B 65/46 |
| 2019/0023298 A1* | 1/2019 | Carzola | B62B 3/10 |
| 2019/0059859 A1* | 2/2019 | Pinch | A61B 8/4405 |
| 2019/0254420 A1* | 8/2019 | Rossini | F16M 11/24 |
| 2019/0270471 A1* | 9/2019 | Hazzard | B25H 1/16 |
| 2019/0290868 A1* | 9/2019 | Heaton | A61M 16/01 |
| 2020/0000430 A1* | 1/2020 | Chamberlain | A61B 8/4254 |
| 2020/0129250 A1* | 4/2020 | Kapadia | A61B 34/30 |
| 2020/0289224 A1* | 9/2020 | Johnson | A61B 34/10 |
| 2020/0290660 A1* | 9/2020 | Wright | F16M 11/22 |
| 2021/0070338 A1* | 3/2021 | Wright | B62B 3/02 |
| 2021/0267707 A1* | 9/2021 | Sung | A61G 12/00 |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Puritan Bennett 980 Series Ventilator Operator's Manual, Covidien, Jan. 29, 2014, Part. No. 10077893 A Jan. 2014, 506 pages.

* cited by examiner

CART FOR MEDICAL EQUIPMENT

CROSS-REFERENCE TO RELATED APPLICATIONS

This application claims priority to and the benefit of the filing date of provisional U.S. Patent Application No. 62/897,079, filed Sep. 6, 2019, the disclosure of which is hereby incorporated herein by reference.

INTRODUCTION

The present disclosure relates to a cart for medical equipment. In patient care facilities such as hospitals, urgent care centers, nursing homes, surgery centers, and other similar facilities, portable carts are used to organize, store, and transport medical equipment. These carts can support lifesaving medical equipment such as mechanical ventilators, resuscitation equipment, surgical tools, vital sign monitors, medication pumps, and other therapeutic medical devices. Carts also support accessories such as breathing circuits, intravenous tubing, catheters, oxygen tanks, bandages, tape, and similar items as needed by the medical caregivers. The remainder of this disclosure addresses improvements in this field.

SUMMARY

This Summary is provided to introduce a selection of concepts in a simplified form that are further described below. In an aspect, the technology relates to a cart for medical equipment, including: a base including one or more wheels; a column supported by the base; a platform supported on the column and opposite the base, wherein the platform is configured to mount a piece of medical equipment to the cart; and an adapter plate securable to the piece of medical equipment and configured to releasably couple to the platform, wherein the adapter plate includes a locking assembly having one or more handles that upon actuation releases the adapter plate from the platform.

In an example, the locking assembly is biased towards a locked configuration that engages the adapter plate to the platform. In another example, the platform includes: a right side and an opposite left side that defines an x-axis; a front and a rear that defines a y-axis; and a top and a bottom that defines a z-axis, and when the adapter plate is engaged with the platform, the adapter plate is secured in the x-axis, the y-axis, and the z-axis directions. In yet another example, the locking assembly actively couples the adapter plate to the platform in the x-axis and the z-axis directions, and the adapter plate is passively coupled to the platform in the y-axis direction. In still another example, the locking assembly includes a slider bar coupled to the one or more handles and a pair of clamp arms coupled to the slider bar, the slider bar is moveable along the y-axis direction upon actuation of the one or more handles, and the pair of clamp arms secure the adapter plate in the x-axis and the z-axis directions. In an example, a pair of handles are disposed on a rear side of the adapter plate and towards each of a right side and a left side of the adapter plate, and each handle of the pair of handles are pivotable about a rotation axis.

In another example, the platform includes a top surface and a projection extending from the top surface, and the projection is configured to engage with the adapter plate. In yet another example, the top surface is substantially devoid of any recesses. In still another example, the platform is configured to tilt relative to the column.

In another aspect, the technology relates to a cart for medical equipment, including: a base including one or more wheels; a column supported by the base; a platform supported on the column and opposite the base, wherein the platform is configured to mount a piece of medical equipment to the cart; and an adapter plate securable to the piece of medical equipment and configured to releasably couple to the platform; and a tilting assembly disposed at least partially within the platform, wherein the tilting assembly includes one or more levers that upon actuation enables the platform to tilt relative to the column and about a tilt axis.

In an example, the tilting assembly is biased towards a locked configuration that prevents tilting of the platform about the tilt axis. In another example, the tilting assembly includes a friction hinge configured to support a weight of the medical equipment mounted on the platform. In yet another example, the tilt axis is disposed proximate a front of the platform. In still another example, the tilting assembly includes a pair of levers disposed on each of a right side and a left side of the platform. In another example, the adapter plate includes a locking assembly having one or more handles that upon actuation releases the adapter plate from the platform.

In another aspect, the technology relates to a cart for a medical ventilator, including: a base including one or more wheels; a column supported by the base; a platform supported on the column and opposite the base, wherein the platform is configured to mount at least a portion of the medical ventilator to the cart, and wherein the platform is selectively tiltable relative to the column about a tilt axis; and an adapter plate securable to the medical ventilator and configured to releasably couple to the platform, wherein the adapter plate includes a locking assembly that is biased so as to automatically engage with the platform.

In an example, the locking assembly includes one or more handles that selectively releases the adapter plate from the platform, and the one or more handles are disposed on a rear side of the cart. In another example, the tilt axis is disposed on a front of the cart, and the one or more handles are opposite of the tilt axis. In yet another example, the adapter plate moves with the platform when it is tilted about the tilt axis. In still another example, the adapter plate includes at least one recessed channel positioned at least partially below the medical ventilator when mounted thereto.

The foregoing general description and the following Detailed Description are exemplary and explanatory and are intended to provide further explanation of the disclosure as claimed.

BRIEF DESCRIPTION OF THE DRAWINGS

The following drawing figures, which form a part of this application, are illustrative of aspects of systems and methods described below.

Specific embodiments have been shown by way of example in the drawings and are described in detail below.

The disclosure is amenable to various modifications and is intended to cover all modifications, equivalents, and alternatives falling within the scope of the disclosure and the appended claims.

DETAILED DESCRIPTION

Although the techniques introduced above and discussed in detail below may be implemented for a variety of medical devices and equipment, some examples will discuss the implementation of these techniques in the context of a medical ventilator for use in providing ventilation support to a human patient. Medical ventilators are used to provide breathing gases to patients who are otherwise unable to breathe sufficiently. A person of skill in the art will understand that the technology described in the context of a medical ventilator for human patients could be adapted for use with other medical devices or equipment.

A cart for medical equipment, such as a ventilator, is described herein. The cart includes an adapter plate that enables the ventilator to be removably coupled to the cart. The adapter plate includes a locking assembly that secures to a platform of the cart and restricts movement and rotation of the adapter plate along three-axes. The locking assembly is automatically biased to as to lock the adapter plate to the platform when coupled thereto. The locking assembly also facilities decoupling of the adapter plate by a technologist from a left or right side of the ventilator. By decoupling the adapter plate from the left or right side, a center of gravity of the ventilator is positioned between the technologist's arms so as to increase ease of lifting. Additionally, patent contacts coupled to a front of the ventilator and power sources coupled to a rear of the ventilator do not need to be contacted. The platform of the cart also includes a tilting assembly that enables the ventilator to be tilted relative to the front of the cart and allow a screen of the ventilator to be visible from multiple angles. The tilting assembly includes a friction hinge that supports the weight of the ventilator so that the tilt angle of the platform can automatically lock in place. A top surface of the platform includes all positive connection features for the locking assembly so that the platform is easier to clean and there are no areas that collect residue.

Figure 1:
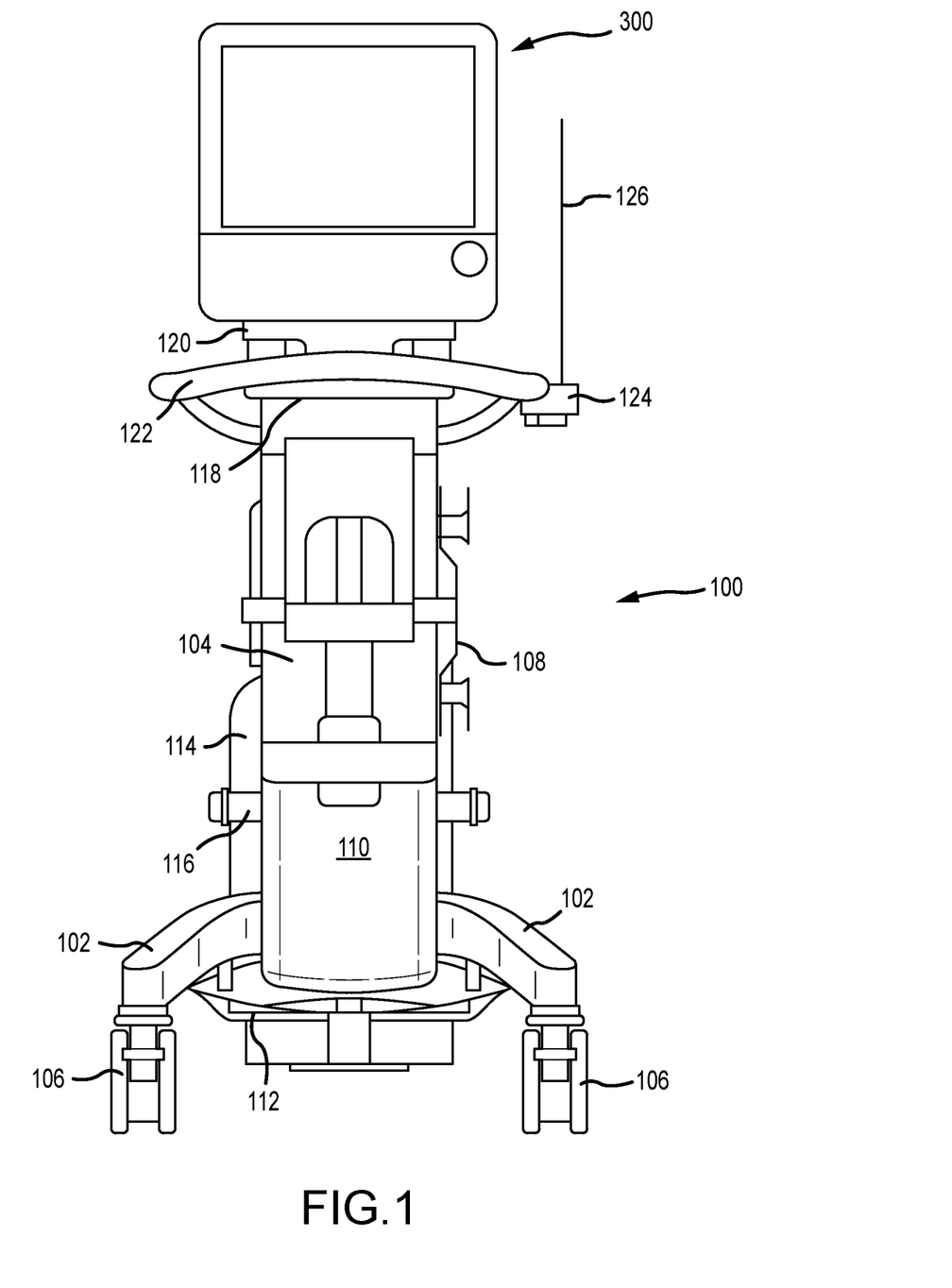
FIG. 1 is front view of a cart for medical equipment according to an embodiment of the disclosure.

FIG. 1 depicts a front view of a cart 100 for medical equipment according to an embodiment of the present disclosure. In the example, the cart 100 is supporting a medical ventilator 300 so that the ventilator 300 and the accompanying accessories may be transported in an efficient and organized manner around the medical care facility. The cart 100 can also support other medical accessories and/or equipment as required or desired. The cart 100 includes a base 102 that supports a column 104. The base 102 rests on a set of wheels or casters 106 that assist in enabling the cart 100 to be moveable around the facility. The column 104 includes various compartments, brackets, clips, and hooks that can hold accessories and tools as required or desired. For example, a bracket 108 may be mounted to a side of the column 104. The column 104 can also include one or more drawers 110 for additional storage. While a single drawer 110 is illustrated in FIG. 1, in other examples, more than one drawer 110 may be included on the cart 100 as required or desired. Additionally, a tank mount assembly 112 is mounted to the base 102 so that one or more gas tanks 114 can be mounted on the cart 100. The tank mount assembly 112 can include any number of bracket, straps, mounts, etc. (e.g., reference number 116) to couple the tanks 114 to the cart 100.

A platform 118 is supported on top of the column 104 and opposite of the base 102. The platform 118 is configured to support the ventilator 300 and allow the ventilator 300 to be removably mounted on the cart 100. An adapter plate 120 is secured to the bottom of the ventilator 300 and is the component that is releasably coupled to the platform 118 so that the ventilator 300 can be selectively taken on and off of the cart 100 as required or desired. As described further below, the adapter plate 120 enables a technologist to efficiently remove and attach the ventilator 300 to the cart 100. The ventilator 300 may weigh about 25 pounds with a center of gravity that is high and in the middle of the ventilator housing. As such, the ventilator 300 can be difficult to remove and attach to the cart 100 without the adapter plate 120. Additionally, the platform 118 enables the ventilator 300 to tilt relative to the column 104 as required or desired by the technologist. The platform 118 and the adapter plate 120 are described in further detail below.

Also, at or near the top of the column 104 and proximate the platform 118, the cart 100 includes a handgrip 122 that fully encircles the top of the column 104 and the platform 118 in an unbroken loop. The handgrip 122 enables the technologist to easily grasp and control the cart 100 from any side (e.g., the front, either side, or the rear) and guide the cart 100 around the medical care facility. In another example, a patient may use the handgrip 122 for assistance while standing. Additionally, the handgrip 122 can also be used to support one or more accessory mounts 124. The accessory mount 124 is positionable at any location on the handgrip 122 and is configured to support various medical accessories, such as a pole 126 (e.g., an IV pole to support an intravenous solution), a circuit mount or support arm (e.g., supporting a breathing circuit such as a tube from the ventilator 300 to a patient), a bar, a hook, a bed mount, a tray, or any other accessory as required or desired.

Figure 2:
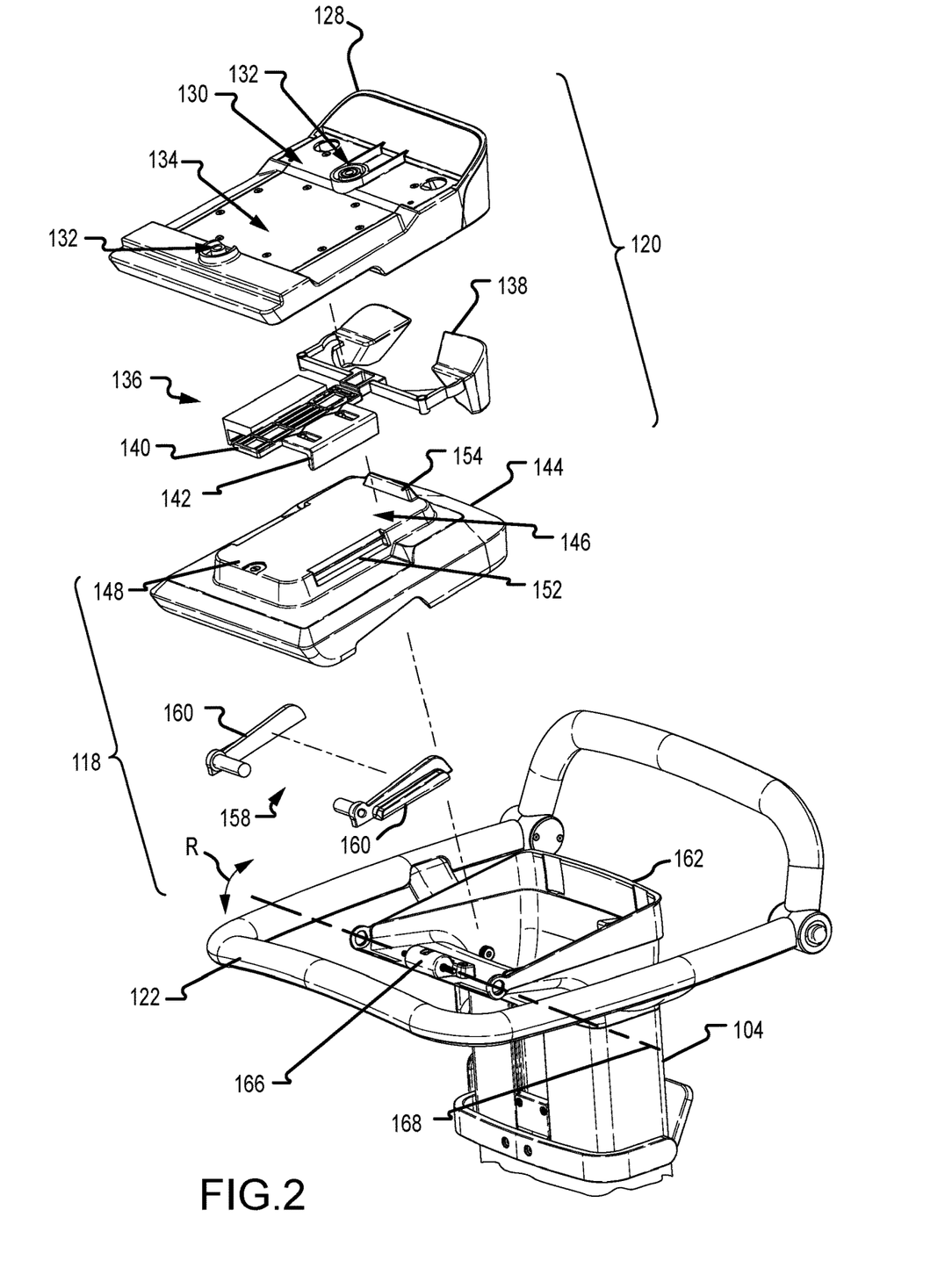
FIG. 2 is an exploded perspective view of a platform and an adapter plate.

FIG. 2 is an exploded perspective view of the platform 118 and the adapter plate 120. The adapter plate 120 includes a plate 128 with a top surface 130 that that the ventilator 300 (shown in FIG. 1) is secured on. For example, a pair of apertures 132 are defined in the plate 128 and can receive threaded fasteners (not shown) that may be used to mount the ventilator to the top surface 130. Additionally or alternatively, any other mounting components that enable the ventilator to be mounted to the top surface 130 may be used as required or desired. The top surface 130 can also include one or more recessed channels 134 defined in the plate 128. In the example, the channel 134 extends from side-to-side and between the apertures 132. The channel 134 is positioned at least partially below the ventilator when it is mounted on the adapter plate 120 so that cooling air flow can be induced towards the bottom of the ventilator and facilitate cooling.

The adapter plate 120 includes a locking assembly 136 that at least partially extends out of the bottom of the plate 128. The locking assembly 136 is configured to selectively engage with the platform 118 so that the ventilator can be securely supported on the column 104. The locking assembly 136 includes a pair of handles 138 coupled to a slider bar 140, and a pair of clamp arms 142 that are coupled to the slider bar 140. The clamp arms 142 are configured to actively engage with the platform 118 so as to couple the adapter plate 120, and thus the ventilator, to the platform 118. When the handles 138 are actuated, the clamp arms 142 disengage from the platform 118 so that the adapter plate 120, and thus the ventilator, can be removed from the platform 118.

The platform 118 has a tilt plate 144 with a top surface 146 that the adapter plate 120 engages with so that the ventilator can be supported on the platform 118. The top surface 146 includes one or more projections 148 extending from the top surface 146 and configured to engage with the adapter plate 120. For example, the projection 148 is substantially rectangular in shape and corresponds to a cavity 150 (shown in FIG. 4) formed underneath the plate 128 of the adapter plate 120. The projection 148 may have a pair of slots 152 that are sized and shaped to engage with the clamp arms 142 of the locking assembly 136, and may include a flange 154 that is sized and shaped to extend within a groove 156 (shown in FIG. 5) formed within the cavity 150 of the plate 128. The top surface 146 of the tilt plate 144 has all positive features (e.g., the projection 148 and the flange 154 extending upwards) so that the top surface 146 may easily be cleaned by the technologist. More specifically, the top surface 146 is substantially devoid of any recesses or negative features so that liquid cleaning solutions are not allowed to accumulate or pool in any areas. This facilitates a more efficient disinfecting process of the top surface 146 by the technologist (e.g., via disinfecting wipes) without any residue accumulation.

The platform 118 includes a tilting assembly 158 disposed at least partially therein. The tilting assembly 158 enables the tilt plate 144 to tilt relative to the column 104. The tilting assembly 158 includes a pair of levers 160 disposed on two opposing sides of the tilt plate 144. In operation, actuation of at least one of the levers 160 (e.g., by the technologist) enables the tilt plate 144 to tilt up and down as required or desired. Additionally, the levers 160 are self-locking so as to lock a tilt angle of the platform 118 relative to the column 104. Because the adapter plate 120 couples to the platform 118, the adapter plate 120 also moves with the platform 118 when the tilt plate is tilted. This tilting motion allows the ventilator that is mounted on the platform 118 to be adjusted as required or desired by the technologist.

The tilting assembly 158 is coupled between the tilt plate 144 and the column 104 and also provides structural support for the tilt plate 144 on the column 104. A tilt axle 166 is supported on the column 104 and disposed proximate a front (e.g., relative to a screen of the ventilator) of the platform 118. The tilt axle 166 defines a tilt axis 168 that the tilt plate 144 rotates R about. By disposing the tilt axis 168 towards the front of the platform 118, when the ventilator is tilted, the movement of the front and bottom portion of the ventilator is reduced or prevented. This area of the ventilator is where the patient connections of the ventilator are located, and by restricting movement of this area of the ventilator, undesirable detachment of patient connections are prevented.

In the example, the tilt axle 166 is coupled to a front underside location of the tilt plate 144 and is a friction hinge. The friction hinge enables the tilt plate 144 to rotate R about the tilt axis 168 and is configured to support the weight of the ventilator so that when the technologist actuates the levers 160, the platform 118 does not drop into its lowest tilt position. Instead, the friction hinge enables the platform 118 to maintain its tilted position until the technologist manually moves the platform 118 in an up or down direction about the tilt axis 168. A skirt 162 is coupled to the top of the column 104 and between the tilt plate 144 and the column 104. The skirt 162 is tapered so that its height is greater towards the rear of the cart than the front of the cart. As such, when the tilt plate 144 tilts, access underneath the tilt plate 144 is prevented.

Figure 3:
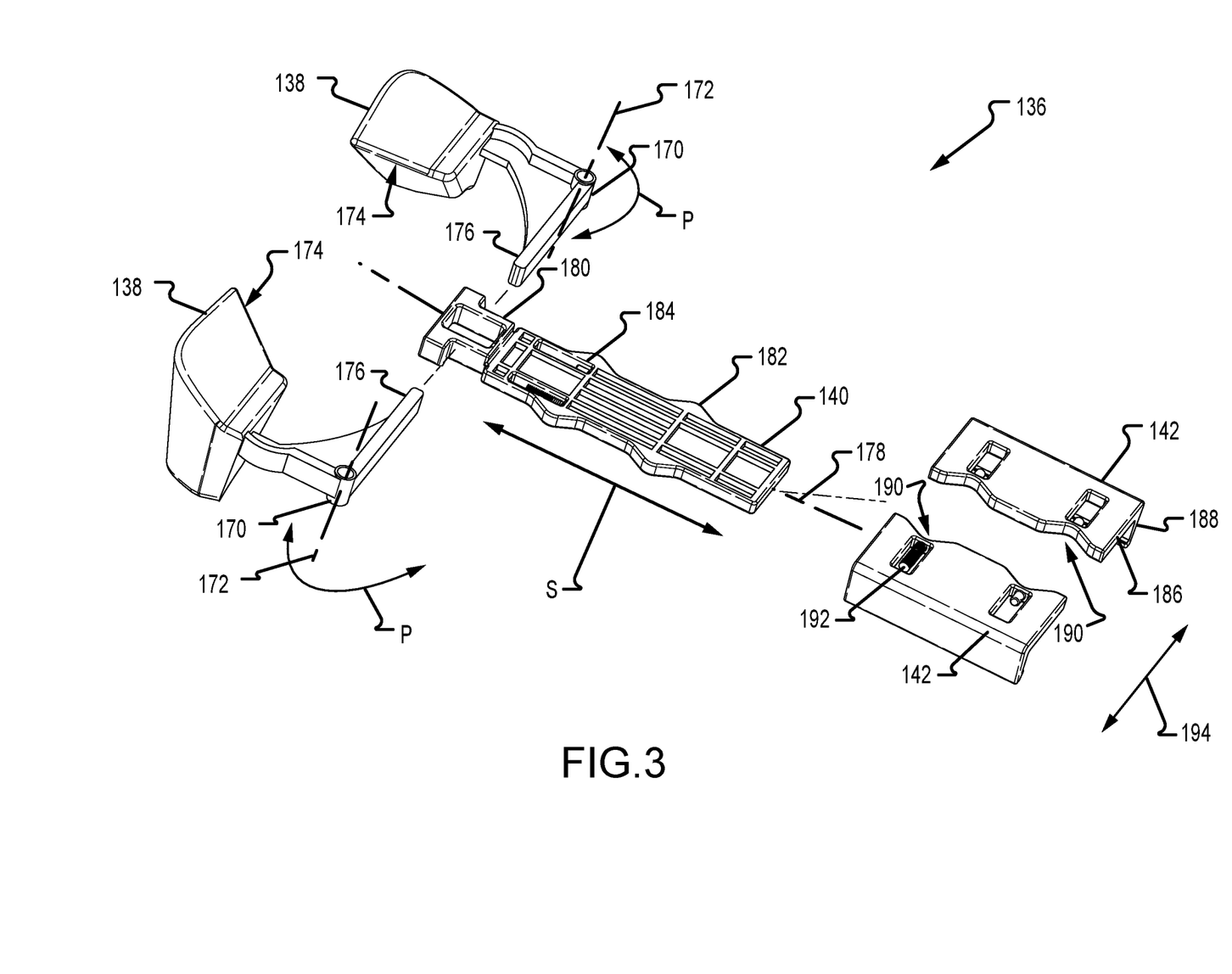
FIG. 3 is an exploded perspective view of a locking assembly of the adapter plate.

FIG. 3 is an exploded perspective view of the locking assembly 136 of the adapter plate 120 (shown in FIG. 2). As described above, the locking assembly 136 includes two handles 138, each coupled to the slider bar 140, and the two clamp arms 142 that are coupled to the slider bar 140. The handles 138 are disposed on the rear of the adapter plate and towards the left side and right side thereof. Each handle 138 is coupled to the plate 128 of the adapter plate (shown in FIG. 2) at a pivot point 170 so that the handles 138 are pivotable relative to the adapter plate. The pivot point 170 defines a rotation axis 172 of the handle 138. Each handle 138 includes an oblique surface 174 that is accessible to the technologist and for actuation of the locking assembly. In the example, the oblique surfaces 174 of each handle 138 face each other. Opposite of the oblique surface 174 and on the other side of the pivot point 170, each handle 138 also includes a rotating arm 176 with a free end that engages with the slider bar 140.

The slider bar 140 is elongated along a sliding axis 178 and includes a head 180 that engages with both of the rotating arms 176 of the handles 138. In the example, the head 180 is substantially T-shaped so that the head 180 can engage with both rotating arms 176 simultaneously. One or more cams 182 extend from both sides of the slider bar 140 (e.g., substantially orthogonal to the sliding axis 178). As illustrated, the slider bar 140 has two cams 182 on either side and spaced apart from each other. The cams 182 may be substantially triangular in shape, or any other shape that enables the locking assembly 136 to function as described herein. Additionally, one or more first biasing elements 184 are coupled between the slider bar 140 and the plate of the adapter plate so as to bias the position of the slider bar 140 along the sliding axis 178.

The slider bar 140 is engaged with the clamp arms 142 and with one clamp arm 142 on either side of the bar 140. Each clamp arm 142 is substantially L-shaped with a cam leg 186 and a hook leg 188. The cam leg 186 includes one or more notches 190 that are shaped and sized to correspond to the cams 182 of the slider bar 140 so that the cam leg 186 is engaged with the slider bar 140. The hook leg 188 is configured to engage with the slot 152 of the platform 118 (shown in FIG. 2) to couple the adapter plate to the platform. Additionally, one or more second biasing elements 192 are coupled between the clamp arm 142 and the plate of the adapter plate so as to bias the position of the clamp arm 142 in a movement direction 194 that is substantially orthogonal to the sliding axis 178.

In operation, the locking assembly 136 is biased towards a locked configuration (e.g., shown in FIG. 4) were the clamp arms 142 are in a retracted position along direction 194 and in a position that couples the adapter plate to the platform. That is, the biasing elements 184 and 192 (e.g., element 184 along the sliding axis 178 and element 192 along direction 194) automatically position the locking assembly 136 so that the cams 182 of the slider bar 140 are within the notches 190 of the clamp arms 142. This engages the hook leg 188 with the platform, when the locking assembly 136 is coupled thereto. To release the locking assembly 136 from the platform, the technologist may actuate one of the handles 138, via the oblique surface 174, to pivot P the handle 138 about the rotation axis 172 and slide S the slider bar 140 along the sliding axis 178 via the corresponding rotating arm 176. As the slider bar 140 slides out of the locked configuration, the cams 182 urge the clamp arms 142 towards an extended position along direction 194 so that the adapter plate can be removed from the platform. Once the handle 138 is released, then the locking assembly 136 automatically returns to the locked configuration via the biasing elements 184 and 192.

Figure 4:
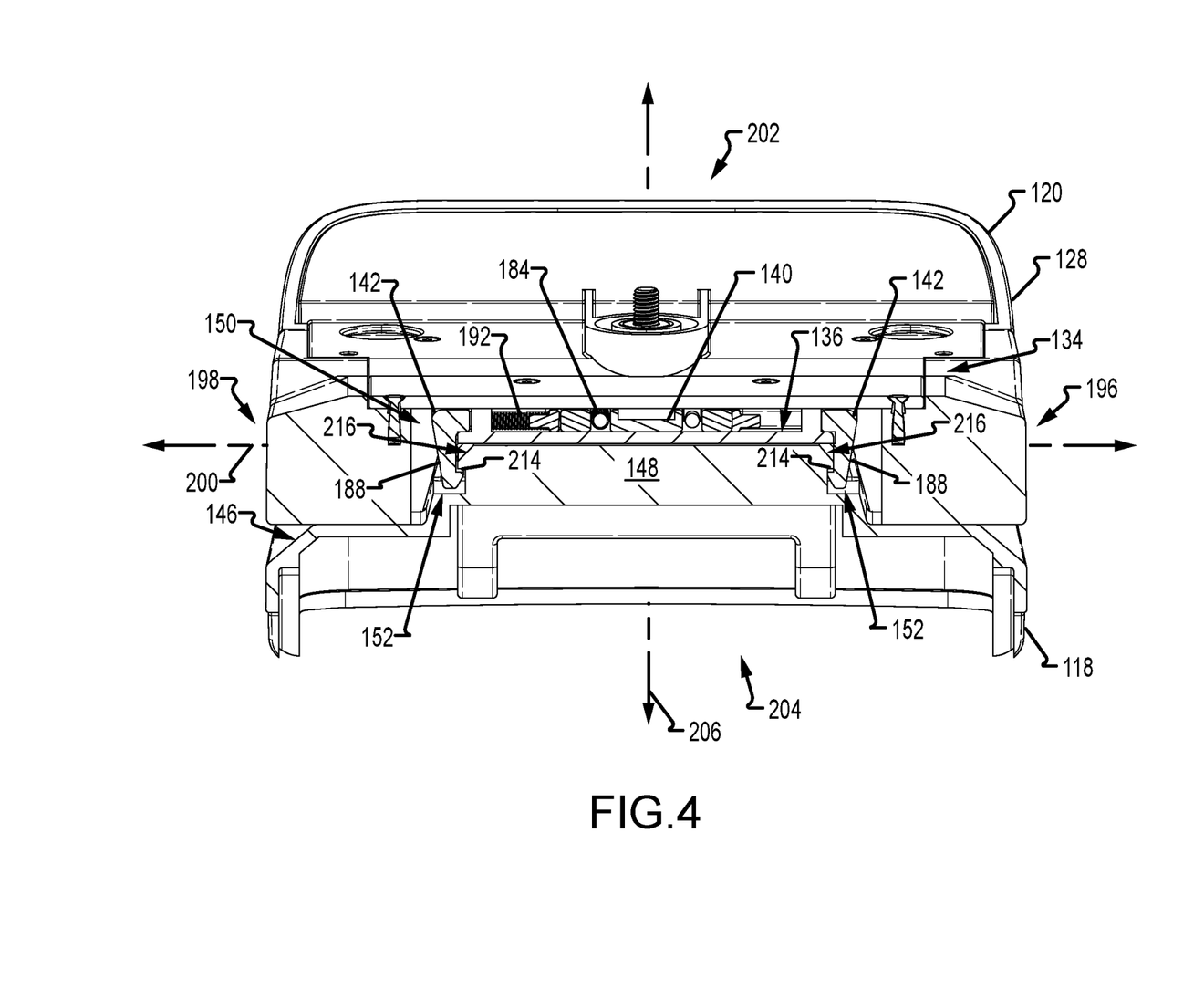
FIG. 4 is a cross-sectional view of the adapter plate coupled to the platform.

FIG. 4 is a cross-sectional view of the adapter plate 120 coupled to the platform 118. As illustrated in FIG. 4, the adapter plate 120 is coupled to the platform 118 and the locking assembly 136 is in a locked configuration so that the adapter plate 120 is prevented from being removed, unless the locking assembly 136 is actively actuated and moved towards a released configuration. The platform 118 has a right side 196 and an opposite left side 198 that defines an x-axis 200 therethrough, a top 202 and an opposite bottom 204 that defines a z-axis 206 therethrough, and a front 208 and a rear 210 (shown in FIG. 5) that defines a y-axis 212 therethrough (e.g., in and out of the page of FIG. 4 and shown in FIG. 5).

When the adapter plate 120 is coupled to the platform 118, the adapter plate 120 is engaged along each of the three axes, the x-axis 200, the y-axis 212, and the z-axis 206. This engagement, secures the adapter plate 120 against movement and rotation in each of the three axes, the x-axis 200, the y-axis 212, and the z-axis 206, so that the ventilator 300 (shown in FIG. 1) is restricted from being removed from the platform 118, unless the locking assembly 136 is actively actuated and moved out of the locked configuration. The locking assembly 136 actively couples the adapter plate 120 to the platform 118 in both of the x-axis 200 and the z-axis 206 directions. As described herein, actively couples refers to the locking assembly 136 being biased to automatically engage with the platform 118 along one or more axes.

The hook leg 188 of the clamp arms 142 are sized and shaped to correspond to the slots 152 in the projection 148 that extends from the top surface 146 of the platform 118. In the x-axis 200 direction, the clamp arms 142 are biased (e.g., by the second basing element 192) so as to compress both hook leg 188 at least partially around the projection 148 and into the slots 152. This engagement of the projection 148 between the clamp arms 142 actively secures the adapter plate 120 in the direction along the x-axis 200. The movement direction 194 of the clamp arms 142 described above in reference to FIG. 3 is substantially parallel to the x-axis 200.

In the z-axis 206 direction, the biasing of the clamp arms 142 also have the hook leg 188 engaged with an undercut surface 214 of the slot 152, and as such, the adapter plate 120 is actively secured in the direction along the z-axis 206. On top of the undercut surface 214, the projection 148 includes tapered surfaces 216 that slope in a downward direction. The tapered surfaces 216 enable the hook legs 188 to automatically extend along the x-axis 200, when the adapter plate 120 is dropped onto the platform 118 and moved in a downward direction along the z-axis 206, so that the technologist does not have to actuate the handles 138 (shown in FIG. 3) to engage the hook leg 188 with the undercut surface 214. As such, the adapter plate 120 can be disposed on top of the platform 118 and have the locking assembly 136 automatically engage with the projection 148. The movement of the clamp arms 142 along the x-axis 200 direction also enables the adapter plate to be automatically positioned on the platform 118 if the locking assembly 136 is not directly aligned with the projection 148. For example, if the locking assembly 136 is rotated about the z-axis 206 up to about 15°, the clamp arms 142 can still engage with the projection 148 and self-center the adapter plate 120 onto the platform 118.

The locking assembly 136 is at least partially disposed within the cavity 150 on the bottom of the plate 128 of the adapter plate 120. The cavity 150 is sized and shaped to receive the projection 148 of the platform 118. As such, when the adapter plate 120 is coupled to the platform 118, access to the locking assembly 136 is prevented, except for the handles 138 (shown in FIG. 3) disposed at the rear of the adapter plate 120. Also illustrated in FIG. 4, the locking assembly 136 includes the slider bar 140 with the first biasing element 184. As described above, the slider bar 140 is moveable along the sliding axis 178 (shown in FIG. 3) and the sliding axis is parallel to the y-axis, which is in and out of the page in FIG. 4. The recessed channel 134 is on the adapter plate 120 so that cooling air flow can be induced towards the bottom of the ventilator 300 (shown in FIG. 1) and facilitate cooling, when the ventilator is mounted thereon.

Figure 5:
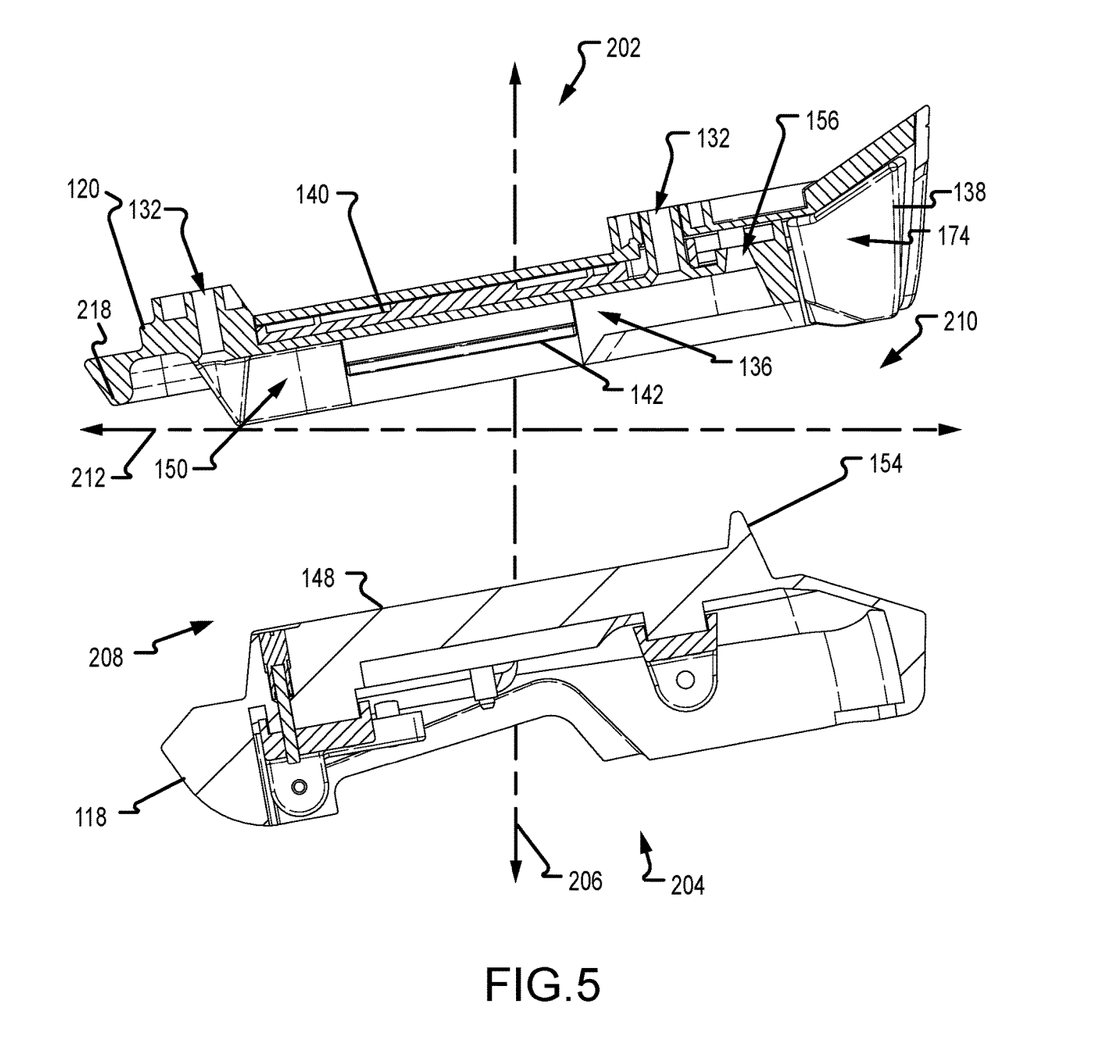
FIG. 5 is a cross-sectional view of the adapter plate removed from the platform.

FIG. 5 is a cross-sectional view of the adapter plate 120 removed from the platform 118. Certain components are described above, and thus, are not necessarily described further herein. To disengage the locking assembly 136 from the projection 148 of the platform 118, the technologist can actuate one handle 138, via the oblique surface 174. Upon actuating the handle 138, the handle 138 pivots around the rotation axis 172 (shown in FIG. 3) and induces movement of the slider bar 140 along a direction along the y-axis 212. The slider bar 140 spreads apart the clamp arms 142 so that the adapter plate 120 can be lifted off of the platform 118 by the technologist. The locking assembly 136 is configured so that the technologist can actuate the handle 138 with one hand and allow for the other hand of the technologist to hold the front part of the adapter plate 120 at a hold 218. Furthermore, the orientation of the oblique surface 174 of the handles 138 directs the technologist to stand on the left or right side of the ventilator 300 (shown in FIG. 1) so that any medical components attached to the front or rear of the ventilator do not need to be contacted.

The support points on the adapter plate 120 (e.g., the hold 218 and the oblique surface 174) increases the efficiency of the technologist coupling and removing the ventilator from the platform 118. With the technologist holding the adapter plate 120 at front and rear locations (e.g., a near rear location and a far front location relative to a side of the adapter plate 120), the technologist is positioned on the left or right side of the adapter plate 120 with the center of gravity of the ventilator placed between the technologist's hands. This configuration makes the ventilator easier and more stable to lift for the technologist. The supports points (e.g., the hold 218 and the oblique surface 174) are also spaced away from the cavity 150 and projection 148 engagement so that pinch points between the adapter plate 120 and the platform 118 for the technologist is reduced.

Additionally, when the adapter plate 120 is coupled to the platform 118 (shown in FIG. 4), the adapter plate 120 is passively coupled to the platform 118 along the y-axis 212. As described herein, passively couples refers to the adapter plate 120 engaging with the platform 118 without any moving components along one or more axes. In this example, the flange 154 of the platform 118 extends in a direction along the x-axis 200 (shown in FIG. 4), and thus, is oriented substantially orthogonal to the y-axis 212. The groove 156 on the adapter plate 120 is sized and shaped to correspond to the flange 154. As such, when the adapter plate 120 is coupled to the platform 118, the flange 154 passively engages with the groove 156, and the adapter plate 120 is secured in the direction along the y-axis 212. The flange 154 and groove 156 engagement also ensures that the adapter plate 120 is oriented in the correct front-rear direction on the platform 118 and the ventilator is coupled to the cart in the correct orientation.

Figure 6:
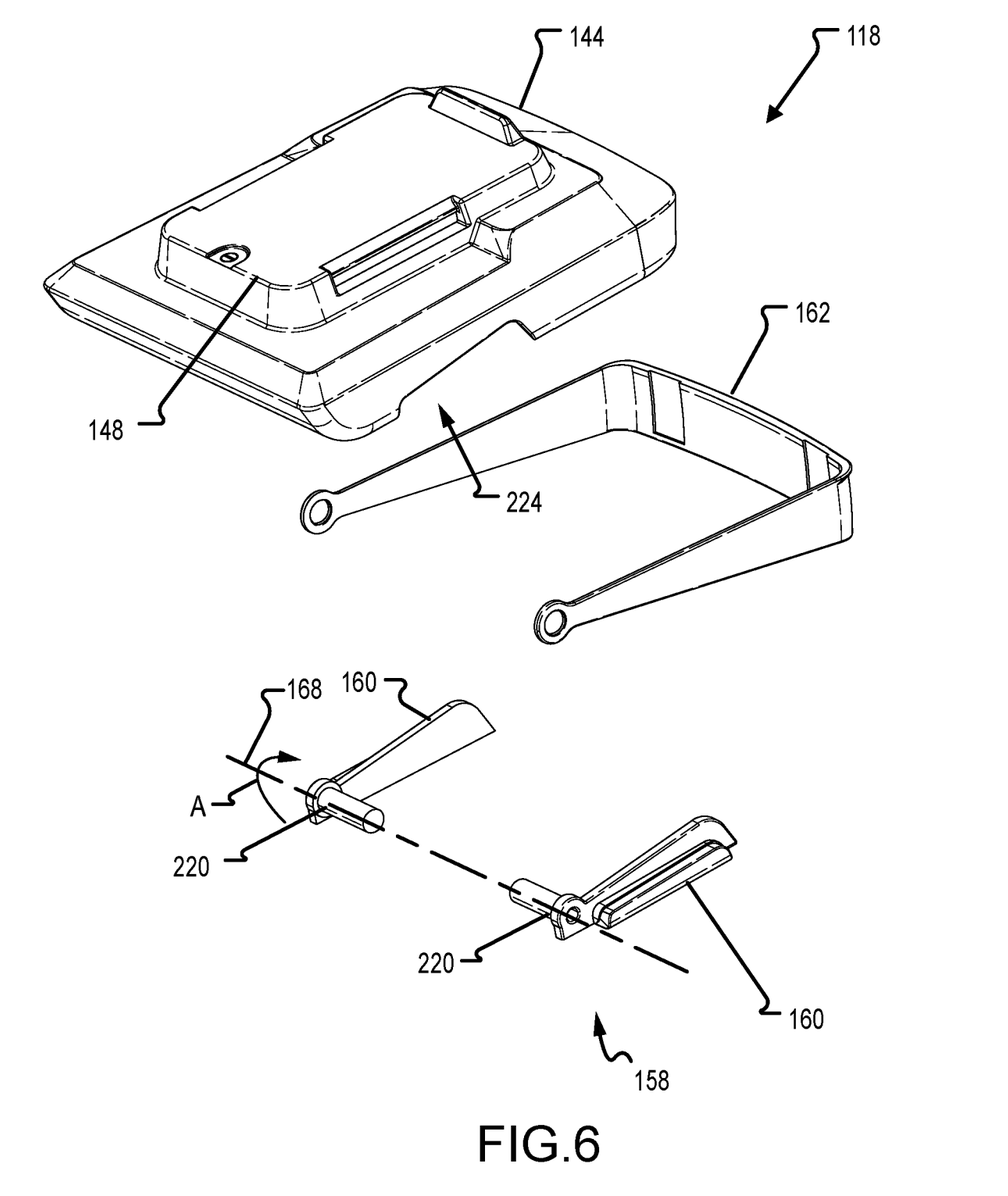
FIG. 6 is an exploded perspective view of the platform.

FIG. 6 is an exploded perspective view of the platform 118. As described above in reference to FIG. 2, the platform 118 has the tilt plate 144 with a projection 148 that releasably couples with the adapter plate 120 (shown in FIGS. 3-5). The tilt plate 144 is tiltably mounted to the top of the column 104 at a tilt axle 166 (both shown in FIG. 2). The skirt 162 is disposed towards the rear of the column and between the top of the column and the bottom of the tilt plate 144. The tilting assembly 158 enables the tilting operation of the platform 118 and includes the pair of levers 160. Each lever 160 is accessible to the technologist and disposed on the right and left sides of the tilt plate 144 at corresponding lever recesses 224. A tilt lock mechanism 220 (schematically illustrated) is coupled to the lever 160 and is positioned between the tilt plate 144 and the column. The tilt lock mechanism 220 is biased so as to automatically move towards a locked configuration that locks the position of the tilt plate 144 relative to the column and so that the tilt plate 144 is prevented from further tilting about the tilt axis 168 unless one of the levers 160 is actuated.

In the example, the levers 160 are actuatable A by the technologist about the tilt axis 168. In an aspect, the lever 160 is actuatable A in an upward direction only so that when the lever 160 is released, the tilt lock mechanism 220 can automatically move towards the locked configuration and the lever 160 is returned to its unactuated position (e.g., in a downward direction). Once the lever(s) 160 is actuated by the technologist, the tilt lock mechanism disengages from its locked configuration so that the technologist can manually move the tilt plate 144 in an up or down direction about the tilt axis 168 and position the ventilator 300 (shown in FIG. 1) as required or desired. As described above, the weight of the ventilator is at least partially supported by the tilt axle acting as a friction hinge. As such, the manual movement of the tilt plate 144 by the technologist does not require the technologist to apply a force that includes the weight of the ventilator, thus facilitating easier tilting movement of the ventilator.

Each lever 160 is coupled to the top of the column and along the tilt axis 168. In the example, the tilt lock mechanism 220 is also coupled to the top of the column along the tilt axis 168. The tilt lock mechanism 220 is configured to rotationally lock the position of the tilt plate 144 about the tilt axis 168 and enable the lever 160 to release the locked configuration. The tilt lock mechanism 220 is also biased so as to automatically return to the locked configuration. In one example, the tilt lock mechanism 220 may include a circumferential rack and a pawl system. In another example, the tilt lock mechanism 220 may include a torsional spring system. In still another example, the tilt lock mechanism 220 may include one or more rotatable lever arms that extend between the column and the tilt plate 144. In some examples, the tilt lock mechanisms 220 may be coupled together so that one-handed tilt operation is enabled. For example, the tilt lock mechanisms 220 may be coupled together by the tilt axle 166 (shown in FIG. 2). Additionally, the tilt lock mechanisms 220 are disposed within the tilt plate 144.

The tilt plate 144 is pivotably coupled to the top of the column at the tilt axle. The tilt axle defines the tilt axis 168, and the tilt lock mechanisms 220 and the levers 160 are disposed on both sides of the tilt axle and along the tilt axis 168. The levers 160 rotate about the tilt axis 168. The tilt axle, and thus the tilt axis 168, is disposed on the front of the column so that the patient connections at the front of the ventilator are restricted from movement during the tilting movement of the platform 118 and to prevent decoupling. The handles 138 of the adapter plate 120 (shown in FIGS. 2-5) are disposed on the rear of the column and opposite from the tilt axis 168.

In operation, the technologist may actuate A one or both of the levers 160, which disengages the tilt lock mechanism 220 from a locked configuration, and enables the technologist to manually move the tilt plate 144 in an up or down direction about the tilt axis 168. In the example, only one lever 160 is required to be actuated A. Additionally, because of the tilt axle acting as a friction hinge, when the lever 160 is actuated A, the platform 118 retains its tilted position until manually moved by the technologist. When the lever 160 is released by the technologist, the tilt lock mechanism 220 automatically moves towards the locked configuration to prevent the platform 118 from tilting about the tilt axis 168, until the levers 160 are again actuated.

The tilt rotation of the tilt plate 144 of the platform 118 may be between about −10° and 40° relative to a horizontal plane. In the example, the platform 118 may tilt about 10° and between about 3° and 13° relative to a horizontal plane. This tilting motion enables the screen of the ventilator to be positioned for various viewing angles.

Numerous changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A cart for medical equipment, comprising:
   a base comprising one or more wheels;
   a column supported by the base;
   a platform supported on the column and opposite the base, wherein the platform is configured to mount a piece of medical equipment to the cart and wherein the platform comprises a top surface and a projection extending from the top surface; and
   an adapter plate securable to the piece of medical equipment and configured to releasably couple to the platform, wherein the adapter plate comprises a locking assembly having one or more handles that upon actuation releases the adapter plate from the platform and wherein the projection is configured to engage with the adapter plate.

2. The cart of claim 1, wherein the locking assembly is biased towards a locked configuration that engages the adapter plate to the platform.

3. The cart of claim 1, wherein the platform comprises:
   a right side and an opposite left side that defines an x-axis;
   a front and a rear that defines a y-axis; and
   a top and a bottom that defines a z-axis, and wherein when the adapter plate is engaged with the platform, the adapter plate is secured in the x-axis, the y-axis, and the z-axis directions.

4. The cart of claim 3, wherein the locking assembly actively couples the adapter plate to the platform in the x-axis and the z-axis directions, and the adapter plate is passively coupled to the platform in the y-axis direction.

5. The cart of claim 3, wherein the locking assembly comprises a slider bar coupled to the one or more handles and a pair of clamp arms coupled to the slider bar, wherein the slider bar is moveable along the y-axis direction upon actuation of the one or more handles, and wherein the pair of clamp arms secure the adapter plate in the x-axis and the z-axis directions.

6. The cart of claim 3, wherein a pair of handles are disposed on a rear side of the adapter plate and towards each of a right side and a left side of the adapter plate, and wherein each handle of the pair of handles are pivotable about a rotation axis.

7. The cart of claim 1, wherein the top surface is substantially devoid of any recesses.

8. The cart of claim 1, wherein the platform is configured to tilt relative to the column.

9. A cart for medical equipment, comprising:
  a base comprising one or more wheels;
  a column supported by the base;
  a platform supported on the column and opposite the base, wherein the platform is configured to mount a piece of medical equipment to the cart; and
  an adapter plate securable to the piece of medical equipment and configured to releasably couple to the platform; and
  a tilting assembly disposed at least partially within the platform, wherein the tilting assembly comprises one or more levers that upon actuation enables the platform to tilt relative to the column and about a tilt axis.

10. The cart of claim 9, wherein the tilting assembly is biased towards a locked configuration that prevents tilting of the platform about the tilt axis.

11. The cart of claim 9, wherein the tilting assembly comprises a friction hinge configured to support a weight of the medical equipment mounted on the platform.

12. The cart of claim 9, wherein the tilt axis is disposed proximate a front of the platform.

13. The cart of claim 9, wherein the tilting assembly comprises a pair of levers disposed on each of a right side and a left side of the platform.

14. The cart of claim 9, wherein the adapter plate comprises a locking assembly having one or more handles that upon actuation releases the adapter plate from the platform.

15. A cart for a medical ventilator, comprising:
  a base comprising one or more wheels;
  a column supported by the base;
  a platform supported on the column and opposite the base, wherein the platform is configured to mount at least a portion of the medical ventilator to the cart, and wherein the platform is selectively tiltable relative to the column about a tilt axis; and
  an adapter plate securable to the medical ventilator and configured to releasably couple to the platform, wherein the adapter plate comprises a locking assembly that is biased so as to automatically engage with the platform.

16. The cart of claim 15, wherein the locking assembly comprises one or more handles that selectively releases the adapter plate from the platform, and wherein the one or more handles are disposed on a rear side of the cart.

17. The cart of claim 16, wherein the tilt axis is disposed on a front of the cart, and wherein the one or more handles are opposite of the tilt axis.

18. The cart of claim 15, wherein the adapter plate moves with the platform when it is tilted about the tilt axis.

19. The cart of claim 15, wherein the adapter plate comprises at least one recessed channel positioned at least partially below the medical ventilator when mounted thereto.

* * * * *